US011460352B2

(12) United States Patent
Zhuang

(10) Patent No.: US 11,460,352 B2
(45) Date of Patent: Oct. 4, 2022

(54) METHOD AND APPARATUS FOR COLLECTING TEMPERATURE OF HEATING PIPELINE

(71) Applicant: BMC Medical Co., Ltd., Beijing (CN)

(72) Inventor: Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 670 days.

(21) Appl. No.: 16/475,315

(22) PCT Filed: Oct. 30, 2017

(86) PCT No.: PCT/CN2017/108418
§ 371 (c)(1),
(2) Date: Jul. 1, 2019

(87) PCT Pub. No.: WO2018/121028
PCT Pub. Date: Jul. 5, 2018

(65) Prior Publication Data
US 2019/0331535 A1 Oct. 31, 2019

(30) Foreign Application Priority Data

Dec. 29, 2016 (CN) .......................... 201611250309.1

(51) Int. Cl.
*G01K 7/16* (2006.01)
*A61M 16/10* (2006.01)
(Continued)

(52) U.S. Cl.
CPC ........... *G01K 7/16* (2013.01); *A61M 16/0875* (2013.01); *A61M 16/1045* (2013.01);
(Continued)

(58) Field of Classification Search
CPC ..... H05B 3/58; A61M 16/0875; A61M 16/10; A61M 16/1045; A61M 16/1095;
(Continued)

(56) References Cited

U.S. PATENT DOCUMENTS 4,708,777 A * 11/1987 Kuraoka ............. F02D 41/1494
123/697
6,586,711 B2 * 7/2003 Whitney ............. G01N 27/4067
219/505
7,385,161 B2 * 6/2008 Smith ................ G01N 27/4067
219/494

FOREIGN PATENT DOCUMENTS

CN 102270000 A 12/2011
CN 102595943 A 7/2012
(Continued)

OTHER PUBLICATIONS

First Office Action dated Nov. 10, 2021 corresponding to European application No. 17888556.2-1001.
(Continued)

*Primary Examiner* — Hung D Nguyen
(74) *Attorney, Agent, or Firm* — Nath, Goldberg & Meyer; Joshua B. Goldberg

(57) ABSTRACT

The present invention discloses is a method for collecting a temperature of a heating pipeline, the method comprising: collecting a circuit signal of a heating resistor; calculating a current resistance value of the heating resistor according to the circuit signal; and calculating a current temperature of the heating pipeline according to the current resistance value. By using the method for collecting the temperature of the heating pipeline, measurement of the temperature of the heating pipeline can be realized by directly measuring the resistance value of the heating resistor in the heating pipeline, which may avoid the use of an additional temperature sensor, thereby reducing the number of connecting wires or other accessories.

17 Claims, 4 Drawing Sheets

(51) Int. Cl.
   *A61M 16/08*   (2006.01)
   *F24H 9/12*   (2022.01)
   *H05B 3/58*   (2006.01)
   *F24H 9/00*   (2022.01)

(52) U.S. Cl.
   CPC .......... *A61M 16/1095* (2014.02); *F24H 9/00* (2013.01); *F24H 9/12* (2013.01); *H05B 3/58* (2013.01); *A61M 2205/3368* (2013.01)

(58) Field of Classification Search
   CPC .. A61M 2205/3368; A61M 2205/6018; A61M 2205/6054; A61M 2205/6072; F24H 9/00; F24H 9/12; G01K 7/16; G01K 15/00
   USPC .......... 219/490, 494, 505, 506, 510
   See application file for complete search history.

(56) References Cited

FOREIGN PATENT DOCUMENTS

| CN | 102791383 A | 11/2012 | | |
|---|---|---|---|---|
| CN | 102958204 A | 3/2013 | | |
| CN | 103558881 A | 2/2014 | | |
| CN | 104049652 A | 9/2014 | | |
| CN | 104116138 A | 10/2014 | | |
| CN | 204742630 U | 11/2015 | | |
| CN | 106840439 A | 6/2017 | | |
| DE | 3802995 A1 | 8/1989 | | |
| DE | 102013000489 A1 | 7/2014 | | |
| DE | 102013000489 A1 * | 7/2014 | ........ | A61M 16/0875 |
| DE | 102013213462 A1 | 1/2015 | | |
| DE | 102013213462 A1 * | 1/2015 | .......... | F02D 41/009 |
| FR | 2935632 A1 | 3/2010 | | |
| TW | 201546455 A | 12/2015 | | |
| WO | 2014/166121 A1 | 10/2014 | | |

OTHER PUBLICATIONS

Search Report dated Dec. 6, 2019 issued in corresponding European Application No. 17888556.2.
First Office Action dated Oct. 22, 2018, in corresponding Chinese application No. 201611250309.1.
Second Office Action dated Jun. 10, 2019, in corresponding Chinese application No. 201611250309.1.
English translation of International Search Report of PCT/CN2017/108418.

* cited by examiner

METHOD AND APPARATUS FOR COLLECTING TEMPERATURE OF HEATING PIPELINE

This is a National Phase Application filed under 35 U.S.C. 371 as a national stage of PCT/CN2017/108418, filed Oct. 30, 2017, an application claiming the benefit of Chinese Application No. 201611250309.1, filed Dec. 29, 2016, the content of each of which is hereby incorporated by reference in its entirety.

FIELD OF TECHNOLOGY

The present invention relates to the field of therapeutic devices, and more particularly, to a method and an apparatus for collecting a temperature of a heating pipeline.

BACKGROUND

A vent pipeline used in a conventional respirator does not include a heating pipeline. Air with a certain humidity (the humidity is to meet the needs of human body for respiratory comfort, and thus dry air is not permitted) is introduced when this type of pipeline is working. Therefore, condensation may occur on the vent pipeline when the ambient temperature is lowered, which may have a negative effect on the respiratory quality. In severe cases, condensate water may flow into a user's respiratory tract through the vent pipeline, which poses a danger to the user's health. Thus, a vent pipeline having a heating function is produced to balance the generation of the condensate water. However, if the pipeline is heated directly, the air to be inhaled into the human body in the vent pipeline may be too high in temperature, which may have a risk of scalding the respiratory tract.

To solve the above problem, in the prior art, generally a temperature sensor is connected to the heating pipeline to control the temperature. However, this method requires an additional separate temperature sensor during the production of the heating pipeline to measure the temperature of the heating pipeline. Following problems exist. Firstly, when the temperature sensor is connected as an accessory to the respirator, an interface needs to be provided to the heating resistor. Furthermore, an interface needs to be provided to the separate temperature sensor, such that a device collects the temperature through the separate temperature sensor, and then performs power control on the heating resistor, which may cause cumbersome processes in the production of products, thereby resulting in excessive overall costs. Secondly, the operation is complex and it is needed to uniquely match parameters such as resistance values and temperatures of all heating resistors in the heating pipelines, which increases production management. In addition, the parameters of heating pipelines need to be entered manually when leaving the factory or replacing the pipelines. In order to solve the above disadvantages, it is particularly important to optimize the temperature control of the heating pipelines.

SUMMARY

On this account, an objective of the present invention is to provide a method and an apparatus for collecting a temperature of a heating pipeline to solve problems in the prior art. By using the method and the apparatus for collecting the temperature of the heating pipeline, measurement of the temperature of the heating pipeline can be realized by directly measuring a resistance value of a heating resistor in the heating pipeline, which may avoid the use of an additional temperature sensor, thereby reducing the number of connecting wires or other accessories.

According to an aspect of the present invention, this application provides a method for collecting a temperature of a heating pipeline, the method including: collecting a circuit signal of a heating resistor during a measurement time period; calculating a current resistance value of the heating resistor according to the circuit signal; and calculating a current temperature of the heating pipeline according to the current resistance value.

According to another aspect of the present invention, this application provides an apparatus for collecting a temperature of a heating pipeline, the apparatus including: a circuit signal collecting module, configured to collect a circuit signal of a heating resistor; a circuit signal processing module, configured to calculate a current resistance value of the heating resistor according to the circuit signal; and a resistance value processing module, configured to calculate a current temperature of the heating pipeline according to the current resistance value.

By using the method the apparatus for collecting the temperature of the heating pipeline provided by the present invention, the problem that a separate temperature sensor needs to be additionally provided to monitor the temperature of a traditional heating pipeline in temperature measurement of the heating pipeline may be solved, periodic measurement of the temperature of the heating pipeline may be implemented by measuring the variation of the resistance value of the heating resistor of the heating pipeline, which may reduce the number of connecting wires or other accessories.

BRIEF DESCRIPTION OF THE DRAWINGS

To describe the technical solutions of the present invention more clearly, the accompanying drawings required for describing the embodiments of the present invention will be briefly introduced below. Apparently, the accompanying drawings in the following description are merely some embodiments of the present invention. To those of ordinary skills in the art, other accompanying drawings may also be derived from these accompanying drawings without creative efforts.

DESCRIPTION OF THE EMBODIMENTS

Preferred embodiments of the present disclosure will be described in more detail below with reference to the accompanying drawings. Although the preferred embodiments of the present disclosure are illustrated in the accompanying drawings, it should be understood that these embodiments are provided so that the present disclosure will be more thoroughly and completely, and the scope of the present disclosure can be fully conveyed to those skilled in the art, and the present disclosure may be implemented in various forms and should not be limited to the embodiments set forth herein.

Embodiment I

Figure 1:
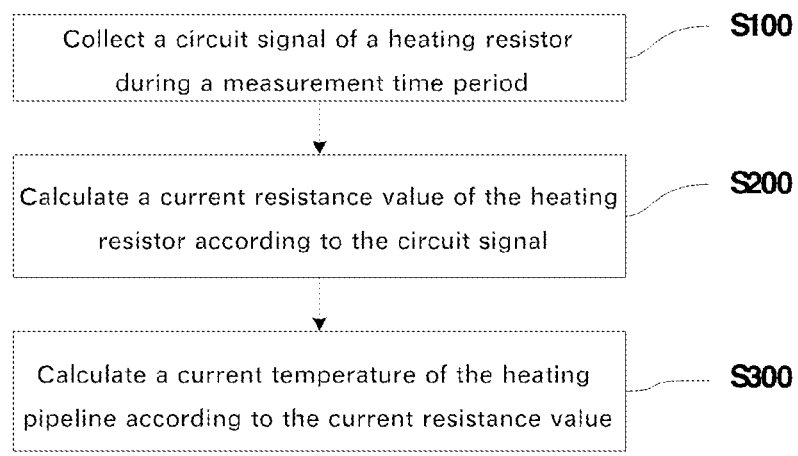
FIG. 1 is a schematic flowchart of a method for collecting a temperature of a heating pipeline according to Embodiment I of the present invention.

This embodiment of the present invention provides a method for collecting a temperature of a heating pipeline, this method being applied to a respirator, which includes: a heating pipeline configured to heat air introduced by the respirator, and a storage module configured to store relevant parameters. Referring to FIG. 1, the method includes the following steps.

Step S100: collecting a circuit signal of a heating resistor during a measurement time period.

Figure 3:
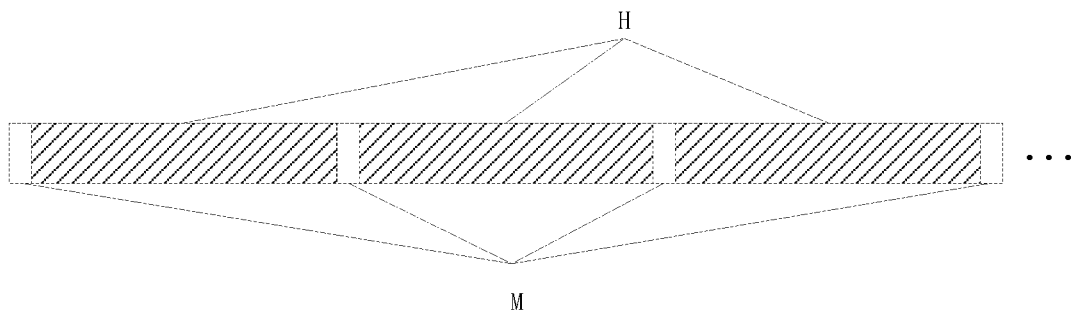
FIG. 3 is a schematic diagram of a working time sequence of a heating time period and a measurement time period of the method for collecting the temperature of the heating pipeline according to Embodiment I of the present invention.

Referring to FIG. 3, for a heating pipeline in the actual application, its normal operation is a process in which a power supply outputs a drive current to heat the heating pipeline (heating time period H). However, according to the method for collecting the temperature of the heating pipeline provided by the embodiment of the present invention, the power output outputs a measurement current (measurement time period M), and this process is embedded in the above heating process. The working time sequence of the heating time period and that of the measurement time period are performed at intervals. The power supply uses a larger output power when outputting the drive current, and the power supply uses a smaller output power when outputting the measurement current.

Step S200: calculating a current resistance value of the heating resistor according to the circuit signal.

In this Step, in the embodiment of the present invention, the power supply may select, for example, a programmable regulating constant current power supply configured to output a constant current, with the output power adjustable. The programmable regulating constant current power supply includes any constant current power supply that may output a corresponding constant current through program control. For different forms of power supplies, the signal collecting module may include, for example, a voltage collecting apparatus or a current collecting apparatus. The collected circuit signal may correspondingly be a current current flowing through the heating resistor or the current voltage of a load. Next, the circuit signal processing module uses the circuit signal (i.e., the current current or the current voltage) collected by the circuit signal collecting module, and obtains the current resistance value $R_c$ of the heating resistor corresponding to the circuit signal based on a relationship between the current, the voltage, and the resistance.

For a preferred embodiment of the present invention, in order to reduce the interference of the output process of the measurement current with the output process of the drive current and to satisfy the measurement of the temperature so as to minimize the effect of the measurement current outputted in the measurement time period on the heating time period, for example, the working time sequence of the heating time period and the working time sequence of the measurement time period may be defined by setting two parameters, wherein the first parameter is a measurement frequency, and the second parameter is a measurement duration. Specifically, the power supply outputs the drive current and the measurement current at intervals according to the measurement frequency, and the measurement duration may be used to limit the length of the output time of the measurement current. The shorter the measurement duration of the measurement current is, the smaller the interference with the output process of the drive current is. The measurement frequency may determine the timeliness of temperature measurement. The higher the measurement frequency is, the higher the timeliness of temperature measurement is, but the greater the impact on the output process of the drive current is. Therefore, appropriate numerical values may be selected for the above two parameters according to actual production requirements.

Step S300: calculating a current temperature of the heating pipeline according to the current resistance value.

Figure 4:
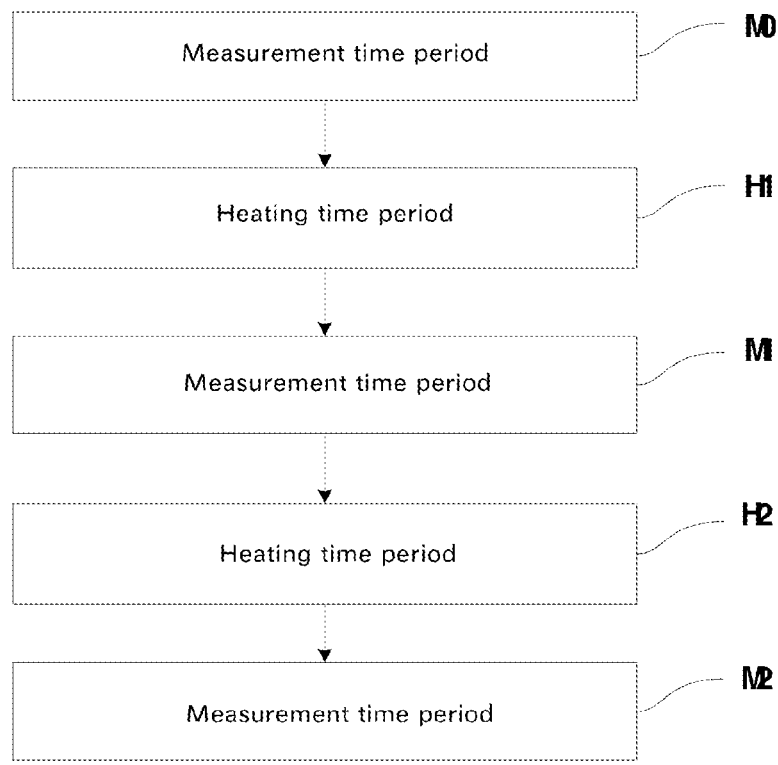
FIG. 4 is a flowchart of the working time sequence of the heating time period and the measurement time period of the method for collecting the temperature of the heating pipeline according to Embodiment I of the present invention.

For this Step, referring to FIG. 4, for example, in the heating time period H1, the power supply outputs a larger drive current to heat the heating pipeline, such that the temperature of the heating resistor gradually rises as time goes on. The resistance value of the heating resistor used by the heating pipeline changes as the temperature changes, and thus the resistance value of the heating resistor also changes, increases generally. After a period of time, the temperature of the heating resistor may stabilize at a value and does not continue to rise. Accordingly, the resistance value of the heating resistor may also stabilize at the value corresponding to the temperature. According to the measurement frequency, when the heating time period H1 ends and enters the measurement time period M1, the power supply outputs a periodical measurement current. Since the measurement duration is short, which is instantaneous, the suddenly introduced measurement current has a very small effect on the temperature of the heating pipeline. When the circuit signal collecting module collects the circuit signal of the heating resistor, the temperature of the heating resistor has hardly changed, and thus the change of the temperature of the heating resistor is negligible.

Therefore, in actual production, it may be approximately believed that the resistance value of the heating resistor also has not changed. In the embodiment of the present invention, the resistance value of the heating resistor calculated out according to the circuit signal measured in the measurement time period M1 is approximately regarded as the current resistance value $R_c$ of the heating resistor in the heating time period H1, and the temperature value of the heating resistor calculated out based on this resistance value is approximately regarded as the current temperature $T_c$ of the heating pipeline in the heating time period H1. Specifically, when the heating pipeline is in a standby state, immediately after the measurement is completed, the output of the measurement current is stopped, such that the heating pipeline is returned to the standby state to ensure safety in use.

Through the above three Steps, the method for collecting a temperature of a heating pipeline provided by the embodiment of the present invention may be implemented in the process of heating the heating pipeline without the need for an external temperature sensor.

Figure 5:
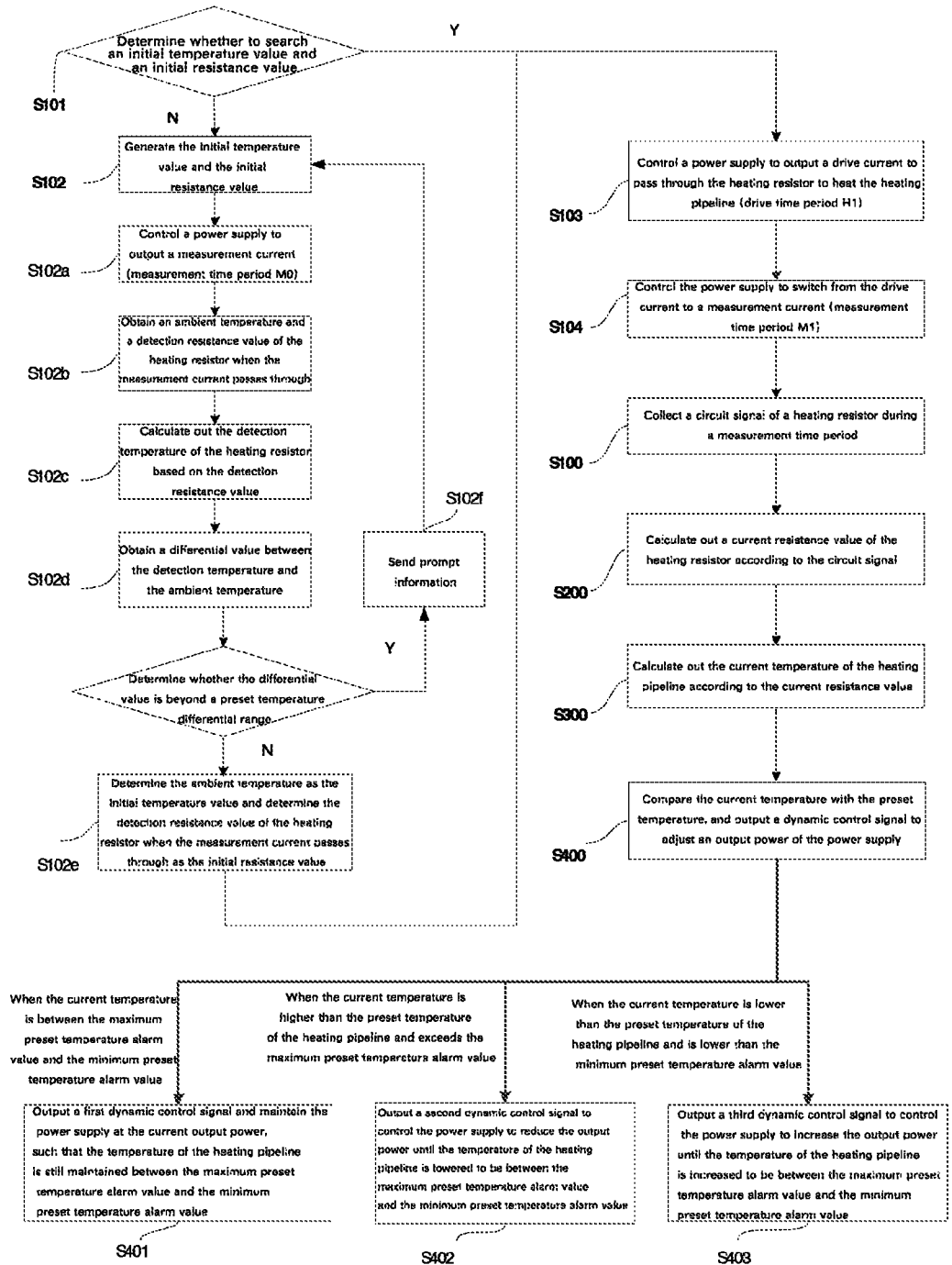
FIG. 5 is a schematic flowchart of the method for collecting the temperature of the heating pipeline containing an automatic recognition process according to Embodiment I of the present invention.

Referring to FIG. 5, in a preferred embodiment of the present invention, before Step S100, the method further includes:

Step S101: searching and determining an initial temperature value of the heating pipeline and an initial resistance value of the heating resistor.

Referring to FIG. 4, the Step of the searching and determining an initial temperature value of the heating pipeline and an initial resistance value of the heating resistor is an automatic recognition process of the heating pipeline. That is, before the heating pipeline starts heating, the power supply is controlled to output a measurement current passing through the heating resistor of the heating pipeline in the measurement time period M0 to determine the initial temperature value $T_0$ and the initial resistance value $R_0$ of the heating pipeline. The programmable regulating constant current power supply may be controlled by a program, such that the constant current power supply outputs the corresponding current required by a loop circuit. Specifically, a larger heating current is outputted in the heating time period, and a smaller measurement current is outputted in the measurement time period.

Specifically, when the initial temperature value and the initial resistance value are obtained, they may be stored in the storage module of the respirator. During the subsequent normal use, after the respirator is started, the initial temperature value and the initial resistance value may be directly obtained from the storage module and may be used, without repeatedly determining the same.

In practical applications, after the heating pipeline is replaced, for a new heating pipeline that is used for the first time, neither the initial temperature value nor the initial resistance value is searched out. In this case, the new heating pipeline needs to be automatically recognized to generate a new initial temperature value and a new initial resistance value and store the same in the storage module.

Therefore, alternatively, when neither the initial temperature value of the heating pipeline nor the initial resistance value of the heating resistor is searched out, the method further includes:

Step S102: generating the initial temperature value of the heating pipeline and the initial resistance value of the heating resistor; and Step 102 includes the following substeps:

Step S102a: controlling a power supply to output a measurement current before the heating pipeline starts heating; that is, the heating pipeline first goes into the measurement time period M0 when the respirator is turned on.

Step S102b: obtaining an ambient temperature and a resistance value of the heating resistor when the measurement current passes through.

Through the above two Steps, the obtained ambient temperature may be determined as the initial temperature value, and the resistance value of the heating resistor when the measurement current passes through may be determined as the initial resistance value.

Preferably, in order to further check whether the heating pipeline is replaced or check whether the heating pipeline is configured, when the respirator is turned on, after the step of determining the initial temperature value of the heating pipeline and the initial resistance value of the heating resistor, a detection step is further included. The detection step includes:

Step S102c: the detection temperature of the heating resistor when the measurement current passes through is obtained.

In this step, a circuit signal of the heating resistor in the measurement time period is collected; a detection resistance value of the heating resistor is calculated out according to the circuit signal; and further, a detection temperature of the heating pipeline is calculated out according to the current resistance value based on the following formula $T_检$:

$$T_检 = \left( \frac{R_c * (T + T_0)}{R_0} - T \right) * K$$

wherein T represents a resistance temperature constant (the value of 235 is taken for a copper wire), and K represents a calibration constant.

Step S102d: calculating a differential value between the detection temperature and the ambient temperature.

Step S102e: when the differential value is within a preset temperature differential range, determining the ambient temperature as the initial temperature value and determining the detection resistance value of the heating resistor when measurement current passes through as the initial resistance value.

Step S102f: sending prompt information when the differential value exceeds the preset temperature differential range.

In the above steps, the power supply outputs a measurement current before the heating pipeline starts heating, the ambient temperature is obtained by using the processing module, meanwhile the detection resistance value of the heating resistor is measured, then the detection temperature of the heating resistor corresponding to the detection resistance value is calculated out by using the detection resistance value, and further, the differential value between the detection temperature and the ambient temperature is calculated out. When the differential value is within the preset temperature differential range, the ambient temperature is determined as the initial temperature value $T_0$, and the detection resistance value of the heating resistor when the measurement current passes through is determined as the initial resistance value $R_0$. When the differential value exceeds the preset temperature differential range, prompt information is sent to prompt that the heating pipeline needs to be adjusted. The preset temperature differential range may be, for example, a range between the minimum preset temperature alarm value $T_{min}$ and the maximum preset temperature alarm value $T_{max}$. Other acceptable temperature ranges are also available for actual production.

It is worth noting that under non-ideal conditions, there should exist a differential value between the ambient temperature and the calculated temperature of the heating pipeline. However, if the differential value is within a preset temperature error range, this is usually acceptable in the actual production. In this case, the ambient temperature may be directly determined as the initial temperature value $T_0$, and the detection resistance value of the heating resistor may be determined as the initial resistance value $R_0$. Otherwise, a prompt is sent to indicate that the heating pipeline may be in an abnormal state. Generally, after the prompt information is sent, a user may decide, according to the actual situation, whether to adjust the heating pipeline or initialize the initial temperature value and the initial resistance value. Once the initialization is performed, Step S102 is repeated to generate the initial temperature value and the initial resistance value.

Step S103: controlling a power supply to output a drive current to pass through the heating resistor, so as to heat the heating pipeline.

After the initial temperature value $T_0$ and the initial resistance value $R_0$ are determined in Step S101, the power supply outputs the drive current to heat the heating pipeline through the heating resistor, i.e., going into the heating time period H1.

Step S104: controlling the power supply to switch from the drive current to a measurement current.

Referring to FIG. 4, the heating time period H1 ends, and when it goes into the measurement time period M1, the power supply is controlled to switch from the drive current to the measurement current. At this moment, the circuit signal collecting module collects the circuit signal of the heating resistor when the measurement current flows through. Reference may be made to Step S100, Step S200 and Step S300 for the subsequent processes to calculate the current temperature of the heating pipeline.

Contents of Step S100 and Step S200 have been described above in detail, and thus their details are omitted herein.

For Step S300, the current resistance value $R_c$ is obtained in Step S200; and after the initial temperature value $T_0$ and the initial resistance value $R_0$ are obtained through the above recognition processes, the process of calculating the current temperature $T_c$ of the heating pipeline may be realized through the following formula:

$$T_c = \left(\frac{R_c * (T \mid T_0)}{R_0} - T\right) * K$$

wherein T represents a resistance temperature constant (the value of 235 is taken for a copper wire), and K represents a calibration constant.

In a preferred embodiment of the present invention, referring to FIG. 5, before Step S100, the method may further include:

Step S400: comparing the current temperature with the preset temperature, and outputting a dynamic control signal according to a comparison result to adjust an output power of the power supply.

Specifically, after the measurement time period M1 ends:

In Step S401, the temperature processing module outputs a first dynamic control signal when the current temperature $T_c$ is between the maximum preset temperature alarm value $T_{max}$ and the minimum preset temperature alarm value $T_{min}$, and the power supply receives the first dynamic control signal and maintains the current output power, such that the temperature of the heating pipeline in the heating time period H2 is still maintained between the maximum preset temperature alarm value $T_{max}$ and the minimum preset temperature alarm value $T_{min}$.

In Step S402, the temperature processing module outputs a second dynamic control signal when the current temperature $T_c$ is higher than the preset temperature of the heating pipeline and exceeds the maximum preset temperature alarm value $T_{max}$, and in the heating time period H2, the power supply receives the second dynamic control signal and reduces the output power until the temperature of the heating pipeline is lowered to be between the maximum preset temperature alarm value $T_{max}$ and the minimum preset temperature alarm value $T_{min}$.

In Step S403, the temperature processing module outputs a third dynamic control signal when the current temperature $T_c$ is lower than the preset temperature of the heating pipeline and is lower than the minimum preset temperature alarm value $T_{min}$, and in the heating time period H2, the power supply receives the third dynamic control signal and increases the output power until the temperature of the heating pipeline is increased to be between the maximum preset temperature alarm value $T_{max}$ and the minimum preset temperature alarm value $T_{min}$.

In the above steps, the output power of the power supply is dynamically monitored by controlling the temperature measured using the method for collecting a temperature of a heating pipeline.

For the embodiments of the present invention, it is to be noted that the circuit signal processing module may select, for example, a proportional-integral-derivative controller (PID controller). The heating pipeline is not specifically described, which includes any vent pipeline having a heating function, for example, a vent pipeline of the respirator. The preset temperature value of the heating pipeline is a preset temperature value, which may be either a determined value or a numerical range as long as it is ensured to be within the preset temperature value range. The temperature of the heating pipeline is an optimum temperature value required for practical applications. A heating mode of the heating pipeline may include a manual heating mode and an automatic heating mode.

As can be seen from the above technical solutions, the present invention includes the following advantages.

By using the method for collecting the temperature of the heating pipeline disclosed by the embodiments of the present invention, measurement of the temperature of the heating pipeline may be realized by directly measuring the resistance value of the heating resistor in the heating pipeline, which may avoid the use of an additional temperature sensor, thereby reducing the number of connecting wires or other accessories.

Specifically, firstly, it is impossible for each of the heating resistors to have an equal resistance value, instead there exists a certain difference therebetween. For example, the resistance value of the heating resistor 2 of the vent pipeline of the respirator is about 40 Ω, the accuracy is ±5%, that is, the deviation is ±2 Ω, and the corresponding converted temperature deviation is ±12° C. If the demand control standard of the vent pipeline of the respirator is less than 43° C., the deviation of ±12° C. cannot meet application demands. If the unique indication of the resistance value and the temperature of the heating resistor is established, this may lead to a great deal of workload in logistics warehouse and production. The initial temperature value $T_0$ and the initial resistance value $R_0$ of the heating pipeline provided in this embodiment may be determined before the heating process begins. Specifically, a reference temperature source used in the present invention is an ambient temperature sensor placed on the respirator. Compared with a traditional heating pipeline whose reference temperature source is placed on the heating pipeline, this temperature sensor is used for reference comparison only when it is powered on to recognize a pipeline. This temperature sensor is not used any more when the respirator is actually running. Instead, the temperature is measured directly based on the resistance variation of the heating resistor itself. In this way, the heating pipeline may be automatically recognized before starting to heat the heating pipeline no matter whether the heating pipeline is configured at the factory or is replaced later. That is, the initial temperature value $T_0$ and the initial resistance value $R_0$ of the heating pipeline are obtained, and low coupling of device components is achieved.

Secondly, considering that the output current of the drive current is larger, the drive current flows through the heating resistor of the heating pipeline to heat the heating pipeline. The large-power drive current may affect the temperature measurement range of the heating pipeline, thereby reducing the measurement precision. The programmable regulating constant current power supply according to this embodiment of the present invention may also output the measurement current within a certain length of time according to a certain frequency during the heating process, and the real-time temperature of the heating pipeline is accurately measured, such that it is avoidable that a larger error may likely be triggered by direct use of the drive current during the measurement.

Thirdly, the power supply of this embodiment adopts the programmable regulating constant current power supply to provide a constant current whose output power is adjustable. The resistance value of the heating resistor of the current heating pipeline may be easily calculated out based on the constant current and the collected voltage value according to the relationship between the current, the voltage and the resistance. Next, the current temperature $T_c$ of the heating pipeline is calculated out, the current temperature $T_c$ is compared with the preset temperature value of the heating pipeline, and a control signal is dynamically outputted to the programmable regulating constant current power supply to implement dynamic adjustment of the heating process.

Embodiment II

Figure 2:
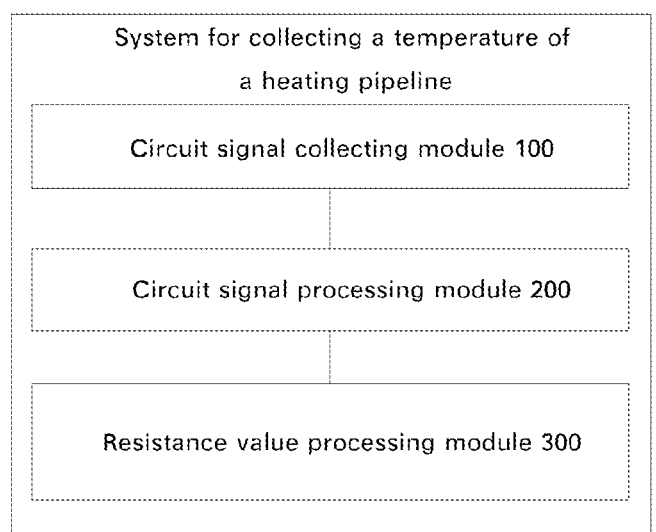
FIG. 2 is a block diagram of an apparatus for collecting a temperature of a heating pipeline according to Embodiment II of the present invention.

This embodiment of the present invention provides an apparatus for collecting a temperature of a heating pipeline. Referring to FIG. 2, the apparatus includes following modules:

a circuit signal collecting module 100, configured to collect a circuit signal of a heating resistor;

a circuit signal processing module 200, configured to calculate a current resistance value of the heating resistor according to the circuit signal; and a resistance value processing module 300, configured to calculate a current temperature of the heating pipeline according to the current resistance value.

Preferably, the apparatus further includes:

a searching module, configured to search and obtain an initial temperature value of the heating pipeline and an initial resistance value of the heating resistor.

Preferably, the apparatus further includes: an initial value generating module, configured to generate an initial temperature value of the heating pipeline and an initial resistance value of the heating resistor.

Preferably, the initial value generating module includes: a first measurement module, configured to control a power supply to output a measurement current before the heating pipeline starts heating; and a module for obtaining an ambient temperature and a resistance value of the heating resistor, configured to obtain the ambient temperature and the resistance value of the heating resistor when the measurement current passes through.

Preferably, after the step of obtaining the ambient temperature and the resistance value of the heating resistor when the measurement current passes through, the apparatus further includes: a calculating module, configured to calculate a temperature value of the heating resistor corresponding to the resistance value by using the resistance value; a differential value calculating module, configured to calculate a differential value between the temperature value and the ambient temperature; an initial value generating submodule, configured to determine the ambient temperature as the initial temperature value when the differential value is within a preset temperature differential range and determine the resistance value of the heating resistor when the measurement current passes through as the initial resistance value; and a prompt module, configured to send prompt information when the differential value exceeds the preset temperature differential range to prompt that the heating pipeline needs to be adjusted.

Preferably, the apparatus further includes: a second heating module, configured to control a power supply to output a drive current to pass through the heating resistor, so as to heat the heating pipeline; and a second measurement module, configured to control the power supply to switch from the drive current to a measurement current.

Preferably, the resistance value processing module includes the following formula:

$$T_c = \left(\frac{R_c * (T + T_0)}{R_0} - T\right) * K,$$

wherein $T_c$ represents the current temperature, $R_c$ represents the current resistance value, $T_0$ represents the initial temperature value, $R_0$ represents the initial resistance value, $T$ represents a resistance temperature constant, and $K$ represents a calibration constant used for calculating the current temperature of the heating resistor.

Preferably, the apparatus further includes: a comparison module, configured to compare the current temperature with the preset temperature, and output a dynamic control signal according to a comparison result to adjust an output power of the power supply.

Preferably, the dynamic control signal includes:

a first dynamic control signal, used for controlling the power supply to maintain the current output power when the current temperature is between a maximum preset temperature alarm value and a minimum preset temperature alarm value, such that the temperature of the heating pipeline is still maintained between the maximum preset temperature alarm value and the minimum preset temperature alarm value;

a second dynamic control signal, used for controlling, when the current temperature is higher than the preset temperature of the heating pipeline and exceeds the maximum preset temperature alarm value, the power supply to reduce the output power until the temperature of the heating pipeline is lowered to be between the maximum preset temperature alarm value and the minimum preset temperature alarm value; and a third dynamic control signal, used for controlling, when the current temperature is lower than the preset temperature of the heating pipeline and is lower than the minimum preset temperature alarm value, the power supply to increase the output power until the temperature of the heating pipeline is increased to be between the maximum preset temperature alarm value and the minimum preset temperature alarm value.

Apparatus embodiments are basically similar to method embodiments, so description of the apparatus embodiments is relatively simple. Please see the method embodiments which may serve as reference.

The flowcharts and the block diagrams in the accompanying drawings illustrate architectures, functions and operations of the apparatus and the method that may be implemented according to a plurality of embodiments of the present invention. In this regard, each block in the flowcharts or block diagrams may represent a module, a program segment, or a code portion. The module, the program segment, or the code portion comprises one or more executable instructions for implementing the specified logical function. It should be noted that, in some alternative implementations, the functions denoted by the blocks may occur in a sequence different from the sequences as shown in the accompanying drawings. For example, in practice, two blocks in succession may be executed, depending on the involved functionalities, substantially in parallel, or in a reverse sequence. It should also be noted that, each block in the block diagrams and/or the flowcharts and/or a combination of the blocks in the block diagrams and/or the flowcharts may be implemented by a dedicated hardware-based system executing specific functions or operations, or by a combination of a dedicated hardware and computer instructions.

It is to be noted that, in the description of the present invention, unless otherwise stated, the sequences, orientations or location relations represented by the terms "first", "second" and "third" or the like are sequences defined artificially or orientations or location relations shown based on the accompanying drawings, they are merely for ease of a description of the utility model or a more clear and organized description instead of being intended to indicate or imply the structure or element to have a special orientation or to be configured and operated in a special orientation. Thus, they cannot be understood as limiting of the utility model.

It is also to be noted that terms such as "comprise", "include" or other variants thereof herein are intended to cover a non-exclusive "comprise" so that a process, a method, a merchandise or a device comprising a series of elements not only includes these elements, but also includes other elements not listed explicitly, or also includes inherent elements of the process, the method, the merchandise or the device. In the case of no more restrictions, elements restricted by a sentence "may include a" do not exclude the fact that additional identical elements may exist in a process, a method, a merchandise or a device of these elements.

It should be understood by those skilled in the art that modules of the device in the embodiments can be adaptively modified and arranged in one or more devices different from the embodiment. Modules, units or components in the embodiment can be combined into one module, unit or component, and also can be divided into more sub-modules, sub-units or sub-components. Except that at least some of features and/or processes or units are mutually exclusive, various combinations can be used to combine all the features disclosed in the specification (comprising claims, abstract and accompanying drawings) and all the processes or units of any methods or devices as disclosed herein. Unless otherwise definitely stated, each of features disclosed in specification (comprising claims, abstract and accompanying figures) may be taken place with an alternative feature having same, equivalent or similar purpose.

The descriptions of the various embodiments of the present invention have been presented above for purposes of illustration, but are not intended to be exhaustive or limited to the embodiments disclosed. Therefore, it is apparent to an ordinary skilled person in the art that modifications and variations could be made without departing from the scope and spirit of the embodiments. The terminology used herein is chosen to best explain the principles of the embodiments, the practical application or technical improvement over technologies found in the marketplace, or to enable others of ordinary skill in the art to understand the embodiments disclosed herein.

What is claimed is:

1. A method for collecting a temperature of a heating pipeline, comprising:
    collecting a circuit signal of a heating resistor during a measurement time period;
    calculating a current resistance value of the heating resistor according to the circuit signal; and
    calculating a current temperature of the heating pipeline according to the current resistance value;
    wherein before the step of collecting a circuit signal of a heating resistor during a measurement time period, the method further comprises:
    measuring and determining an initial temperature value of the heating pipeline and an initial resistance value of the heating resistor;
    after the step of determining the initial temperature value of the heating pipeline and the initial resistance value of the heating resistor, the method further comprises a detection step, the detection step comprising:
    calculating a detection temperature of the heating pipeline;
    calculating a differential value between the detection temperature and an ambient temperature;
    continuing to determine the ambient temperature as the initial temperature value and determine the detection resistance value of the heating resistor when the measurement current passes through as the initial resistance value when the differential value is within a preset temperature differential range; and
    sending prompt information when the differential value exceeds the preset temperature differential range.

2. The method according to claim 1, wherein when neither the initial temperature value of the heating pipeline nor the initial resistance value of the heating resistor is searched out, the method further comprises:
    generating the initial temperature value of the heating pipeline and the initial resistance value of the heating resistor.

3. The method according to claim 2, wherein the step of generating the initial temperature value of the heating pipeline and the initial resistance value of the heating resistor comprises:
    controlling a power supply to output a measurement current before the heating pipeline starts heating;
    obtaining an ambient temperature and a resistance value of the heating resistor when the measurement current passes through; and
    determining the ambient temperature as the initial temperature value and the resistance value of the heating resistor as the initial resistance value.

4. The method according to claim 3, wherein after the step of determining the initial temperature value of the heating pipeline and the initial resistance value of the heating resistor, the method further comprises a detection step, the detection step comprising:
    collecting a detection circuit signal of the heating resistor;
    calculating a detection resistance value of the heating resistor according to the detection circuit signal;
    calculating a detection temperature of the heating pipeline according to the detection resistance value;
    calculating a differential value between the detection temperature and the ambient temperature;
    continuing to determine the ambient temperature as the initial temperature value and determine the detection resistance value of the heating resistor when the measurement current passes through as the initial resistance value when the differential value is within a preset temperature differential range; and
    sending prompt information when the differential value exceeds the preset temperature differential range.

5. The method according to claim 1, wherein, the step of calculating a detection temperature of the heating pipeline comprises:
    collecting a detection temperature of the heating pipeline comprises:
    calculating a detection resistance value of the heating resistor according to the detection circuit signal;
    calculating a detection temperature of the heating pipeline according to the detection resistance value.

6. The method according to claim 1, wherein before the step of collecting a circuit signal of a heating resistor during a measurement time period, the method further comprises:
controlling a power supply to output a drive current to pass through the heating resistor, so as to heat the heating pipeline; and
controlling the power supply to switch from the drive current to a measurement current.

7. The method according to claim 6, wherein the step of calculating a current temperature of the heating pipeline according to the current resistance value comprises:
calculating the current temperature of the heating pipeline based on a formula as below:

$$T_c = \left(\frac{R_c * (T + T_0)}{R_0} - T\right) * K,$$

wherein $T_c$ represents the current temperature, $R_c$ represents the current resistance value, $T_0$ represents the initial temperature value, $R_0$ represents the initial resistance value, T represents a resistance temperature constant, and K represents a calibration constant.

8. The method according to claim 1, wherein after the step of calculating a current temperature of the heating pipeline according to the current resistance value, the method further comprises:
comparing the current temperature with a preset temperature and outputting a dynamic control signal according to a comparison result to adjust an output power of the power supply.

9. The method according to claim 8, wherein, the step of comparing the current temperature with the preset temperature, and outputting a dynamic control signal according to a comparison result to adjust an output power of the power supply comprises:
outputting a first dynamic control signal when the current temperature is between a maximum preset temperature alarm value and a minimum preset temperature alarm value to control the power supply to maintain the current output power, such that the temperature of the heating pipeline is maintained between the maximum preset temperature alarm value and the minimum preset temperature alarm value;
outputting a second dynamic control signal when the current temperature is higher than the preset temperature of the heating pipeline and exceeds the maximum preset temperature alarm value to control the power supply to reduce the output power until the temperature of the heating pipeline is lowered to be between the maximum preset temperature alarm value and the minimum preset temperature alarm value; and
outputting a third dynamic control signal when the current temperature is lower than the preset temperature of the heating pipeline and is lower than the minimum preset temperature alarm value to control the power supply to increase the output power until the temperature of the heating pipeline is increased to be between the maximum preset temperature alarm value and the minimum preset temperature alarm value.

10. The method according to claim 1, wherein in the step of calculating a current temperature of the heating pipeline according to the current resistance value, a temperature of the heating resistor gradually rises as time goes on, and after a period of time, the temperature of the heating resistor stabilizes at a value and does not continue to rise, and a resistance value of the heating resistor also stabilizes at the value corresponding to the temperature.

11. The method according to claim 1, wherein in the measurement time period a power supply outputs a measurement current, and in a heating time period, the power supply outputs a drive current to heat the heating pipeline,
wherein the working time sequence of the heating time period and that of the measurement time period are performed at intervals.

12. An apparatus for collecting a temperature of a heating pipeline, comprising:
a memory having instructions stored thereon;
a processor configured to execute the instructions to perform operations, comprising:
collecting a circuit signal of a heating resistor;
calculating a current resistance value of the heating resistor according to the circuit signal; and
calculating a current temperature of the heating pipeline according to the current resistance value;
wherein the operations further comprise;
generating an initial temperature value of the heating pipeline and an initial resistance value of the heating resistor,
wherein the operation of generating an initial temperature value of the heating pipeline and an initial resistance value of the heating resistor comprises;
calculating a detection temperature of the heating pipeline;
calculating a differential value between the detection temperature and an ambient temperature;
continuing to determine the ambient temperature as the initial temperature value and determine the detection resistance value of the heating resistor when the measurement current passes through as the initial resistance value when the differential value is within a preset temperature differential range; and
sending prompt information when the differential value exceeds the preset temperature differential range.

13. The apparatus according to claim 12, wherein the operations further comprise:
measuring and determining an initial temperature value of the heating pipeline and an initial resistance value of the heating resistor.

14. The apparatus according to claim 13 wherein the operations further comprise:
controlling a power supply to output a drive current to pass through the heating resistor, so as to heat the heating pipeline; and
controlling the power supply to switch from the drive current to a measurement current.

15. The apparatus according to claim 13, wherein the operation of generating an initial temperature value of the heating pipeline and an initial resistance value of the heating resistor comprises:
controlling a power supply to output a measurement current before the heating pipeline starts heating;
obtaining an ambient temperature and the resistance value of the heating resistor when the measurement current passes through; and
determining the ambient temperature as the initial temperature value and the resistance value of the heating resistor as the initial resistance value.

16. The apparatus according to claim 15, wherein the operation of calculating a detection temperature of the heating pipeline comprises comprises:
- collecting a detection circuit signal of the heating resistor;
- calculating a detection resistance value of the heating resistor according to the detection circuit signal;
- calculating a detection temperature of the heating pipeline according to the detection resistance value.

17. The apparatus according to claim 12 wherein the operations further comprise
- comparing the current temperature with a preset temperature and outputting a dynamic control signal according to a comparison result to adjust an output power of the power supply.

* * * * *